United States Patent [19]

Lewicky

[11] 4,331,130

[45] May 25, 1982

[54] SECURING DEVICE TO THE CORNEA TO PREVENT ANTERIOR CHAMBER PROLAPSE

[76] Inventor: Andrew O. Lewicky, 2716 Blackhawk Rd., Wilmette, Ill. 60091

[21] Appl. No.: 163,518

[22] Filed: Jun. 27, 1980

[51] Int. Cl.³ .................... A61B 19/00; A61M 7/00
[52] U.S. Cl. ............................ 128/1 R; 128/249; 128/305
[58] Field of Search ............... 128/276, 305, 349 R, 128/1 R, 277, 278, 273, 249, 348; 433/81, 84

[56] References Cited

U.S. PATENT DOCUMENTS 1,688,795  10/1928  Aas .................................. 128/348

OTHER PUBLICATIONS

Abstract, "Ein Kurzer Uberlick uber den Fortsuhritt der Behandluns perforierender Verletzunsen des Auses", Klin Monatsbl Ausonheilkd, Oct. 1979, vol. 175, (4), pp. 447-452, Issn OO23-2165.

"The Use of Anterior Chamber Na-Hygluronate in a Pseudophakic Patient Requiring Intravitreal Air During Retinal Reattachment Surgery", Swartz, M. D. et al., Opthalmic Surgery, vol. 12, No. 2, Feb. 1981, pp. 98–99.

"Vitrectomy Instrumentation for Surgical Evacuation of Total Anterior Chamber Hyhema and Control of Recurrent Anterior Chamber Hemorrhage", Stern, M. D. et al., Opthalmic Surgery, vol. 10, No. 1, Jan. 1979, pp. 34-37.

"Maintenance of the Anterior Chamber in Intraocular Surgery: Instruments and Techniques", Page, Jr., M. D. et al., Transactions of the Pacific Coast Oto-Ophthalmological Society, 1968.

"New Fiat Air Injection Chamber", Note, Cases and Instruments Am. Journal of Opthalmology, vol. 86, No. 6, Dec. 1978.

Primary Examiner—Robert W. Michell
Assistant Examiner—J. L. Kruter
Attorney, Agent, or Firm—Thomas W. Tolpin

[57] ABSTRACT

An apparatus and method to prevent collapse of the anterior chamber of the eye during ophthalmic surgical procedures. The apparatus has an infusion terminal with external threads or detents which snap fit into interlocking engagement with the eye without the use of sutures. One or more pumps are pneumatically and hydraulically connected to the infusion terminal via a series of tubes to selectively inject air, saline solution and other liquids into the anterior chamber of the eye during the surgical procedure. The apparatus can be remotely operated by the surgeon with a foot pedal to minimize the amount of surgical assistance needed during the procedure. The infusion terminal can also be Y-shaped for attachment to separate air and liquid containing tubes or can have an annular abutment flange to limit the extent to which the infusion terminal can enter the eye.

10 Claims, 7 Drawing Figures

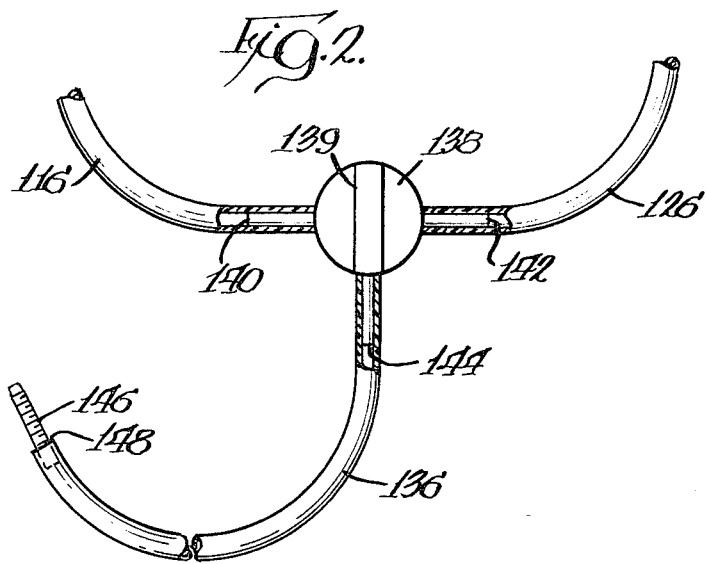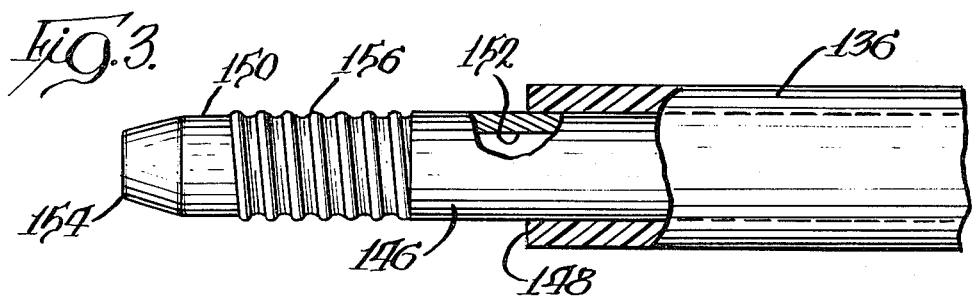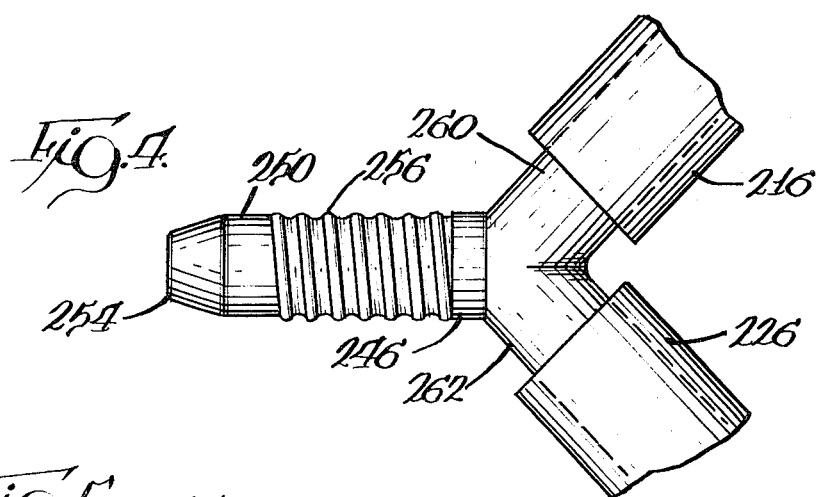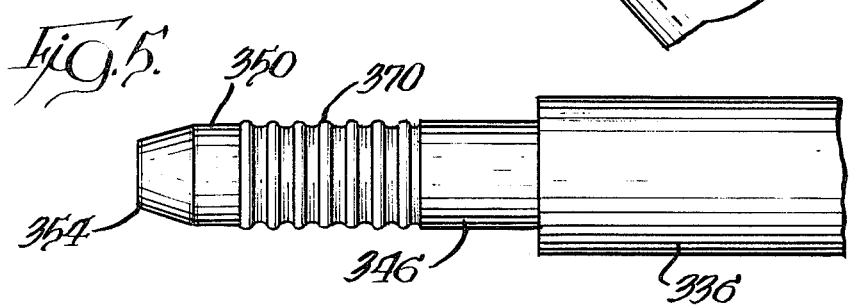

SECURING DEVICE TO THE CORNEA TO PREVENT ANTERIOR CHAMBER PROLAPSE

DESCRIPTION

Technical Field of the Invention

This invention relates to ophthalmic surgical procedures, and more particularly, to a method and apparatus for preventing collapse of the anterior chamber of the eye.

BACKGROUND OF THE INVENTION

During various types of ophthalmic surgical procedures, it is very difficult to maintain the normal configuration of the anterior chamber of the eye. Frequently, the anterior chamber of the eye will collapse during surgical entry into the eye. Collapse of the anterior chamber of the eye and failure to keep the anterior chamber in an uncollapsed state substantially increases the difficulty of various surgical maneuvers and may result in irreversible damage to the vital corneal endothelial cells causing permanent corneal edema and consequent blurred vision.

In the past, various pre-operative methods and operative methods have been attempted to alleviate this problem. These prior art methods have met with varying degrees of success.

In one pre-operative method, osmotic agents are systemically administered to the patient in an attempt to shrink the fluid component of the vitreous humor to reduce the overall volume of the vitreous. When the vitreous volume is reduced, there is less tendency for the anterior chamber of the eye to decompress.

In another pre-operative method, external compression forces are applied to the eyeball and eye socket tissues by massaging or the like before surgical entry is made to effectively reduce the fluid volume of the orbital tissues and the eye so as to reduce the intraocular volume and periocular orbital tissue pressure.

Various prior art operative methods require complete anesthesia and akinesia of the ocular muscles inasmuch as contraction of the eye muscles are transmitted to the eyeball once surgical entry has been made. General anesthesia with nondepolarizing muscle relaxant has been used as has local injectable agents.

In an effort to minimize eyelid pressure which could be transmitted to the sclera, various eyelid speculum devices have been used to keep the eyelids open during surgery. Sometimes, the eyelid opening has to be surgically enlarged to reduce eyelid pressure.

In another operative method, the fluid component of the vitreous is aspirated through a separate entry site to decompress the eye volume. This method, however, may lead to retinal complications and vitreous hemorrhage.

In other prior art techniques, infusion terminals or external metal rings have been sutured to the eye in an effort to alleviate the above problems, but suturing requires additional surgical time and effort, necessitates additional sutural entries into the eye and is not always effective.

It is therefore desirable to provide an improved method and apparatus to prevent collapse of the anterior chamber of the eye.

SUMMARY OF THE INVENTION

An improved method and apparatus is provided for preventing collapse of the anterior chamber of the eye during ophthalmic surgical procedures. The method and apparatus are effective, efficient and reliable, and can be easily and readily used under the expert independent control of the surgeon.

The novel apparatus has a specially configured infusion terminal which is inserted into the eye. The infusion terminal is connected, such as by medical grade tubing, to one or more pumps. The pumps pump air and physiologically acceptable saline solution or other liquids into the anterior chamber of the eye to maintain positive pressure and normal configuration of the anterior chamber during surgery.

In the preferred form, the infusion terminal has a shank and cornea-engaging external threads or other detents, such as annular rings. The infusion terminal can be single bored if connected to a single tube or can be Y-shaped with twin bores if connected to two tubes, such as an air inlet tube and a liquid inlet tube.

While the novel apparatus of this invention can be used with various ophthalmic surgical procedures, one preferred method of using the apparatus includes making an incision into the cornea of the eye to form an opening spanning a distance slightly more than the maximum diameter of the external threads or rings of the infusion terminal. After the opening in the eye has been formed, the infusion terminal is inserted into the opening so that the threads or rings snap fit into interlocking engagement with the eye to securely connect the infusion terminal to the eye without the need of sutures. The threads of the infusion terminal can also be screwed into the eye opening if desired.

A more detailed explanation of the invention is provided in the following description and appended claims taken in conjunction with the accompanying drawings.

BRIEF DESCRIPTION OF THE DRAWINGS

FIG. 2 is an enlarged fragmentary cross-sectional view of portions of the anterior chamber maintainer;

FIG. 3 is a greatly enlarged perspective view of the infusion terminal in accordance with the principles of the present invention;

FIG. 4 is a perspective view of a Y-shaped infusion terminal in accordance with principles of the present invention; and FIG. 5 is a perspective view of a ribbed infusion terminal in accordance with principles of the present invention;

DETAILED DESCRIPTION OF THE PREFERRED EMBODIMENTS

Figure 1:
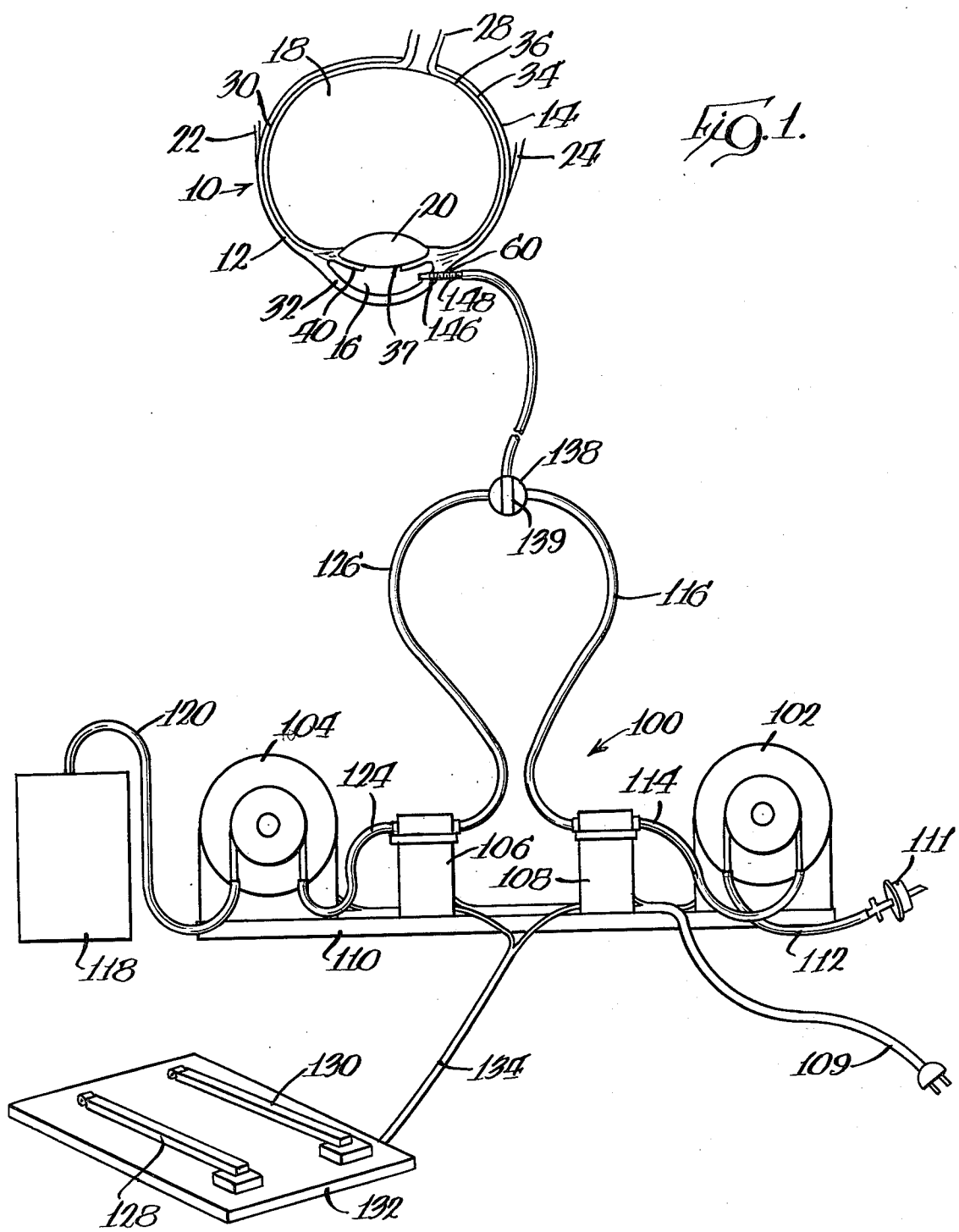
FIG. 1 is a perspective view of an anterior chamber maintainer and an enlarged cross-sectional view of an eye which has been connected to an infusion terminal of the anterior chamber maintainer in accordance with the principles of the present invention.

In order to best understand and appreciate the invention, it is best to first have a basic understanding of the physiological components of the eye 10. As shown in FIG. 1, the eyeball 12 is basically a hollow sphere, the walls 14 of which are made of a fairly tough but flexible tissue. The anterior chamber 16 of the eye provides a space or cavity which is located between the cornea 32 and the lens 20. The anterior chamber 16 is bounded in front by the cornea 32 and is bounded in back by the lens 20 and iris 40. The anterior chamber 16 of the eye contains a physiologic fluid while the vitreous humor 18 located behind the lens 20 contains a combination fluid-gel. The eyeball 12 itself is located within a rigid bony socket and is surrounded by soft tissues and fat. Attached to the eyeball are major muscles 22 and 24 (and others not shown), nerves 28 and blood vessels 30. The muscles control the movement of the eye. These muscles include the lateral rectus muscle 24, the medial rectus muscle 22, the superior rectus muscle, the inferior and superior oblique muscles and tendon, and the inferior rectus muscle. The arteries of the eye include the short ciliary, the long ciliary and the anterior ciliary, as well as the central artery of the retina 36. The nerves attached to the eye include the optic nerve 28 as well as the long and short ciliary nerves. Posteriorly, the fibers of the optic nerve 28 enter through small perforations in the lamina cribrosa.

The eyeball or oculus 12 is generally sphere-shaped with coats: the sclera 14 or external coat, which is white and fibrous, the cornea 32 in front, the choroid 34 and the retina 36 or internal coat. The coats are divided into several layers and surround refracting media such as the aqueous humor 37, the crystalline lens 20 and the vitreous humor 18. The aqueous humor 37 is located between the cornea 32 and lens 20. The vitreous humor 18 is a clear, jelly-like substance containing mucin which fills the space behind the lens 20. The lens 20 is a double convex transparent body between the vitreous and aqueous humors 18 and 37 which is held in place by an elastic capsule and suspensory ligament.

The cornea 32 is comprised of five layers: the endothelial cell layer, Descemet's membrane, stroma, Bowman's membrane and epithelial cells.

The retina 36 or internal coat of the eye is composed chiefly of nerve tissue. The external layer of the retina is composed of terminal nerve cells in the form of rods and cones.

The iris 40 provides a curtain with a central perforation. The pupil is composed of smooth muscular fibers arranged in a circular and radiating manner. The iris varies in color and is suspended in the aqueous humor 37 in front of the lens 20. The iris 40 is surrounded by the ciliary ligament as well as by the ciliary muscle 26 which controls the convexity of the lens 20.

In accordance with the principles of the present invention, an anterior chamber maintainer, apparatus or device 100 (FIG. 1) is provided so as to prevent the anterior chamber 16 from collapsing during ophthalmic surgery. Anterior chamber maintainer 100 injects air, saline solution, viscous fluid material such as is sold under the brand name Healon, or other liquid or gaseous fluids into the anterior chamber 16 of the eye to increase the internal pressure of the anterior chamber 16 so as to counterbalance and offset the usual compressive forces that are exerted on the anterior chamber during ophthalmic surgery. The anterior chamber maintainer 100 can be completely operated under the expert independent control of the surgeon with minimal or no assistance from others.

As shown in FIG. 1, anterior chamber maintainer 100 has a pneumatic pump 102 and a fluid or liquid pump 104 which are controlled by optional solenoid valves 106 and 108, respectively. Solenoid valves 106 and 108 are powered by power line 109. In the illustrative embodiment, both pumps 102 and 104 are peristaltic pumps and are supported upon a platform or base 110. Pneumatic pump 102 pumps air which has passed through a filtering device 111 via tube 112 into air lines or tubes 114 and 116 at a selected flow rate and pressure. Fluid pump 104 pumps medical grade saline solution or other liquid from container 118 via tube 120 into liquid containing lines or tubes 124 and 126. The flow rate and pressure of the pumps 102 and 104 are remotely controlled by the surgeon through foot pedals 128 and 130, respectively of a control panel 132 via a control line 134. The pressure can also be automatically controlled through an optional feed-bath circuit with a pressure sensitive regulator for sensing the pressure of the eye.

Tubes 126 and 128 are connected to an outlet infusion line or tube 136 via a tri-tube valve connector, such as a T-connector or three way stop cock 138 with connection terminals 140, 142 and 144 (FIG. 2) and a pivotable control handle 139. Tubes 112, 114, 116, 120, 124, 126 and 136 are made of medical grade silicone elastomer tubing, such as is sold by Dow Corning under the trademark Silastic. In the preferred set up, the parts and components of the anterior chamber maintainer 100 are arranged to minimize dead space within the tubes so that the maintaining system 100 can rapidly change from liquid infusion to air infusion without drawing in unwanted gas or fluids lodging in the dead space of the tubing.

As shown in FIGS. 1–3, an eye-engaging self-retaining infusion terminal 146 is connected to the outlet end 148 of infusion tube 136. Infusion terminal 140 provides a cannula with a shank 150 (FIG. 3) and an axially extending central fluid-flow passageway 152 for passage of air, liquids and other fluids into the eye. Shank 150 has a tapered rounded head 154. Infusion terminal 140 is made of finely polished stainless steel or other metal, but other materials can also be used, such as impact-resistant medical grade plastic.

One of the many important aspects of this invention is the provision of eye-engaging, self-retaining connection means along the shank 150 of infusion terminal 146. In the embodiment shown in FIG. 3, the eye-engaging connection means take the form of helical external screw threads 156 which extend outward from shank 150. The externally threaded infusion terminal 146 is inserted into a surgical opening into the eye, such as in the cornea, to securely engage and connect the infusion terminal to the eye without the need of sutures. The threads provide removal deterring means which substantially deter accidental removal of the infusion terminal from the eye during ophthalmic surgical procedures.

The Y-shaped infusion terminal 246 of FIG. 4 is similar to the infusion terminal 146 of FIG. 3 except that Y-shaped infusion terminal 246 (FIG. 4) has an air inlet 260 connected to the air tube 216 and has a liquid inlet 262 connected to the liquid containing tube 226. This embodiment eliminates the need for an outlet tube 136 (FIG. 2) and a tri-tube connector 138 (FIG. 2). For ease of understanding and clarity, similar parts and components of infusion terminal 246 (FIG. 4) have been given numbers similar to the parts and components of infusion terminal 146 (FIG. 3), but in the 200 series, such as shank 250, threads 256, etc.

The infusion terminal 346 shown in FIG. 4 is similar to the infusion terminal shown in FIG. 2, except that the eye-connection means of infusion terminal 246 have annular detents, rings, or circular ribs 370 in lieu of threads 156 (FIG. 3) which extend circumferentially outward of shank 350. For ease of understanding and clarity, similar parts and components of infusion terminal 346 (FIG. 5) have been given numbers similar to parts and components of infusion terminal 146 (FIG. 3), but in the 300 series, such as shank 350, etc.

In the embodiments shown in FIGS. 3-5, the maximum outside diameter of the threads 156, 256 or detents 370, as well as the shank 150, 250 or 350 span a distance slightly smaller than the surgical opening, i.e., slightly smaller than the diameter of a circular surgical opening or slightly smaller than the width of an oblong surgical opening, to snap-fittingly interlockingly engage the portions of the eye surrounding the opening. The pliable elastic tissue portions of the eye about the opening swell and contract about and securely engage the threads or detents after the infusion terminal has been inserted into the opening.

Figure 6:
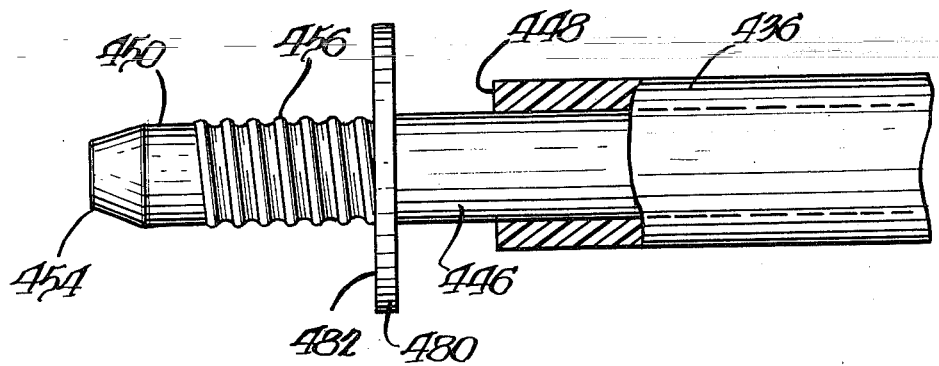
FIG. 6 is a perspective view of a threaded infusion terminal with an annular flange in accordance with the principles of the present invention.

Referring to the embodiment of FIG. 6, the infusion terminal 446 of FIG. 6 is similar to the infusion terminal 146 of FIG. 3, except that it has an annular abutment flange or base plate 480 which extends circumferentially outward of shank 450 and threads 456. Flange 480 is located rearwardly and upstream of threads 456 and has an eye-engaging front surface 482. Flange 480 limits the extent to which infusion terminal 446 can be inserted into the eye and is useful in pars plana procedures. For such procedures, the infusion terminal 446 of FIG. 6 should have a larger diameter and length than infusion terminal 146 of FIG. 3. For ease of understanding and clarity, similar parts and components of infusion terminal 446 have been given numbers similar to the parts and components of infusion terminal 146 (FIG. 3) but in the 400 series, such as shank 450, threads 456, etc.

While the above embodiments are preferred, in some circumstances it may be desirable that the eye-engaging connection means take the form of one or more radial spokes or detents that extend outward of the shank.

While the anterior chamber maintainer of FIGS. 1-5 can be used in many ways to perform a variety of ophthalmic surgical procedures, the preferred method includes making a small tract incision or puncture through the cornea 32 to form an infusion terminal-receiving opening 60 (FIG. 1) that is slightly larger than the maximum outside diameter of the threads or rings. As shown in FIG. 1, after the opening 60 has been made, the end of the infusion terminal 146 is inserted into the anterior chamber 16 of the eye via the infusion terminal-receiving opening 60 in cornea 32 until at least one of the helical threads 156 or rings 370 (FIG. 5) has entered into the interior of the cornea so that the threads or rings snap-fit and wedge against the cornea in press-fitting interlocking engagement to detachably secure and clamp the infusion terminal to the eye without the use of sutures. Afterwards, a saline solution, viscous fluid, or air is injected into the anterior chamber 16 of the eye at the desired pressure and the remainder of ophthalmic surgical procedure is performed by the surgeon. At the end of the surgical procedure, the infusion terminal is removed by gently but firmly withdrawing the terminal from the eye. In one surgical procedure, a 21 gauge needle was used to make an infusion terminal-receiving opening in the cornea and a 23 gauge externally threaded infusion terminal was connected to that opening. Of course, other gauge sizes can be used.

It may also be desirable in some circumstances to screw the threads of the infusion terminal into the infusion terminal-receiving opening of the cornea. Such a procedure has been accomplished with a 22 gauge needle and a 23 gauge threaded infusion terminal. It is preferred that the opening of the eye be one gauge size larger than the helical threads for threaded engagement therewith, but be two gauge size larger than the helical threads or rings if the threads or rings are to simply snap-fit into the cornea.

The anterior chamber maintainer can be employed in various types of ophthalmic surgical procedures to maintain the normal configuration of the anterior chamber 16 of the eye. The anterior chamber maintainer is particularly useful for anterior segment surgery, such as in the following ophthalmic procedures:

1. aspiration and irrigation of soft cataracts such as congenital cataracts and traumatic cataracts;
2. planned extra-capsular cataract extraction in adults with or without intraocular lens implantation;
3. adult intracapsular cataract extraction with or without intraocular lens implantation;
4. various surgical manipulations involving anterior segment surgery usually with the presence of a preexisting intraocular lens such as relocation of a dislocated intraocular lens, suturing of intraocular lens loop to the iris (McCannel suture placement), amputation of intraocular lens loops, discission of secondary membranes following intraocular lens implantation;
5. secondary intraocular lens implantation;
6. penetrating keratoplasty (corneal transplants) with or without intraocular lens implantation or pre-existence;
7. certain glaucoma filtration procedures such a trabeculectomy; and
8. ultrasonic fragmentation of cataracts.

All of the above procedures have in common the desirability of maintaining the anterior chamber during the surgical procedure. The actual mechanics of the use of the anterior chamber maintainer instrument is similar in all the above cases with minor variations and the surgeon's discretion of the use of either liquid or air.

For example, the procedure for planned adult extracapsular cataract extracation with intraocular lens implantation can be carried out under general or local anesthesia. The aid of an operating microscope is mandatory. After anesthetic induction of the patient, the eye is draped in standard fashion. The anterior chamber maintainer is prepared by the circulating and scrub nurses. The prepackaged sterile tubing is obtained and one line 112 is attached to a millipore air filter 111. Tubing 114 and 124 are connected to the solenoid on/-off valves 108 and 106 and pump inlet lines 112 and 118, respectively. The sterile end 148 of the outlet infusion tube 136 with the threaded self-retaining infusion terminal 146 is then brought into the surgical field.

The patient having been previously prepped and draped in the usual fashion and anesthetized properly is now ready for the surgical procedure. The operating microscope is placed into position. A lid speculum is inserted and a superior rectus traction suture is placed under the superior rectus tendon. A fornix based conjunctival flap is dissected. The limbus is cleaned with a Gill knife. Hemostasis is controlled with cautery. A continuous corneal scleral groove is made from approximately the 10 to 2 o'clock position along the superior surgical limbus. Two 8-0 silk sutures are pre-placed in this partial thickness groove. A 22 gauge disposable needle attached to a TB syringe is then used to create a corneal tract inferiorly in the 6 o'clock meridian. This corneal tract is a full thickness tract entering the anterior chamber. The needle is withdrawn.

Pump 104 is activated and the fluid line is filled with balanced salt solution. The initial speed setting of the pump is in the low mode setting. The 23 gauge infusion terminal 148 filled with balanced salt solution is now placed through this corneal tract at the 6 o'clock position. The infusion terminal is self-retaining and places little pressure on the globe of the eye. The thin light weight outlet infusion tubing 136 attached to the infusion terminal 148 is placed to the side of the surgical field, out of the surgeon's way. The surgeon now has complete control over the depth of the anterior chamber 16 by way of infusion of either fluid or air through the pump mechanism of the anterior chamber maintainer which is controlled by foot operated pedals 128 and 130 under the surgeon's control.

The anterior chamber is then entered at the 11 o'clock position with a razor blade knife. Afterwards, the cystotome is inserted and a 360 degree anterior capsulotomy is performed while the chamber depth is controlled by the anterior chamber maintainer. The anterior capsule is removed from the eye with fine capsule forceps. The nucleus of the cataract is loosened within its capsule with the cystotome. The corneal section is then enlarged to approximately 160 degrees and the nucleus of the cataract is prolapsed from the anterior chamber. There are various techniques of prolapsing the nucleus of the cataract and it should be pointed out that prolapsing of this nucleus is made easier by the presence of the infusion terminal 146 at the 6 o'clock position. The flow of balanced salt solution at the time of prolapsing of the nucleus actually aids in floating the nucleus out from the anterior chamber.

The two pre-placed silk sutures are now tied and the residual cortical material remaining in the eye is aspirated from the anterior chamber 16 with a 3 cc syringe to which is attached a 25 or 27 gauge Olive tipped Cannula. The syringe is managed by the surgeon's two hands giving him complete control over aspiration, as well as reflexing of the aspirated material. Throughout this aspiration, the depth of the anterior chamber 26 is maintained with the anterior chamber maintainer under the surgeon's control utilizing infusion of balanced salt solution.

In cases where there is a significant amount of vitreous pressure, it may be necessary to place one or more additional sutures to close the incision in order to prevent excessive out flow of fluid from the anterior chamber. A tight surgical wound during the aspiration irrigation phase of this procedure is actually desirable because it reduces the overall amount of fluid used during this stage of the surgical procedure. It is believed that less damage is suffered by the corneal endothelial cells when the amount of irrigation fluid is reduced. In those cases where closure of the wound fails to maintain proper chamber depth, the rate of infusion can be increased.

After all of the residual cortical cataractous material has been aspirated from the eye, the posterior capsule is cleaned and polished with diamond dusted capsule polishing instruments. Afterwards, the anterior chamber is filled with air via air infusion pump 102 and lines 112, 114 and 116 by the surgeon's activation of the air pedal 128. The air injected into the anterior chamber will displace and eject the salt solution out of the eye.

The intraocular lens which has been previously chosen by the surgeon and prepared in a fashion well known in the art is now ready for insertion. It is important to maintain the normal configuration of the anterior chamber and prevent the delicate corneal endothelial cells on the inside of the cornea from touching the front surface of the intraocular lens during the actual insertion of the implant. This can be achieved by positive pressure infusion via the anterior chamber maintainer during the actual insertion stage. By utilizing positive pressure infusion, it is possible to safely insert intraocular lenses even in patients who have high vitreous pressures or whose anterior chambers tend to collapse under surgical entry.

After the intraocular lens has been placed in the proper position, the cornescleral incision is closed with sutures. The conjunctiva is likewise sutured closed. The infusion terminal 146 is then removed from the corneal tract. The residual air is aspirated with a 30 gauge cannula and replaced with balanced salt solution. The corneal tract is closed with one interrupted 10-0 nylon suture which is removed after 24 hours.

The use of air or fluid is dictated by the particular stage of the specific surgical procedure in question and to some degree by the individual surgeon's preference in certain situations where either air or fluid can be utilized. For example, during irrigation and aspiration of residual cataractous cortical material, only liquid need by used, whereas during the insertion of an intraocular lens, either liquid or air can be utilized depending on the tendency for the anterior chamber to collapse.

The technique employed for maintaining the anterior chamber during the other various surgical procedures described above is essentially similar to the procedures discussed above for adult extracapsular cataract surgery, that is, the infusion terminal is inserted through a corneal tract as previously described and the anterior chamber is maintained by the surgery with either liquid or air via control pedals 128 and 130.

Figure 7:
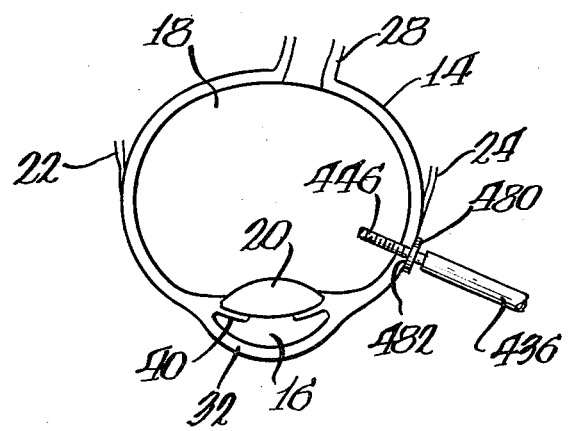
FIG. 7 is a cross-sectional view of the eye connected to the infusion terminal of FIG. 6.

The infusion terminal can also be inserted into other surgically made infusion terminal-receiving openings in the eye other than the cornea 32, such as through the sclera 14 during pars plana lensectomies or vitrectomies to maintain the globe of the eye during posterior segment surgery as shown in FIG. 7. In the embodiment of FIG. 7, the eye-engaging front surface 482 of flange or base 480 abuts against the sclera 14 and serves as an abutment stop to limit the extent to which infusion terminal 446 can be inserted into the vitreous humor 18 of the eye. In one procedure, a 23 gauge infusion terminal with a base was used to perform a pars plana vitrectomy. Other size infusion terminals can also be used.

Although embodiments of the invention have been shown and described, it is to be understood that various modifications and substitutions as well as a rearrangement of parts and steps can be performed by those skilled in the art without departing from the novel spirit and scope of this invention.

What is claimed is:

1. An opthalmic apparatus for substantially preventing collapse of the anterior chamber of an eye during anterior segment surgery and for substantially maintaining the globe of the eye during pars plana lensectomies and vitrectomies in posterior segment surgery, comprising: pneumatic pump means for pumping air into an eye, liquid pump means for pumping saline solution and other liquids into said eye, and eye-engaging and securing infusion terminal means for insertion into the corona of said eye during anterior segment surgery and into the sclera of said eye during pars plana lensectomies and vitrectomies, and fluid-flow connection means for simultaneous connecting of said pneumatic and liquid pump means to said eye-engaging infusion terminal.

2. An apparatus in accordance with claim 1 wherein said fluid-flow connection means includes first tube means connected to said pneumatic pump means and second tube means connected to said liquid pump means, and said eye-engaging infusion terminal includes a Y-shaped terminal having a first inlet connected to said first tube means and a second inlet connected to said second tube means.

3. An apparatus in accordance with claim 1 wherein said fluid-flow connection means includes first tube means connected to said pneumatic pump means, second tube means connected to said liquid pump means, third tube means connected to said eye-engaging terminal and tri-tube connection means connecting said third tube means to said first tube means and to said second tube means.

4. An apparatus for substantially preventing collapse of the anterior chamber of an eye during ophthalmic surgical procedures, comprising:
pneumatic pump means for pumping air into the anterior chamber of an eye;
liquid pump means for pumping saline solution and other liquids into the anterior chamber of the eye;
an eye-engaging infusion terminal for entering into the cornea of said eye and communicating with said anterior chamber, said eye-engaging infusion terminal having a shank and cornea-engaging connection means extending outward of said shank for connecting said infusion terminal to the cornea of said eye; and
fluid-flow connection means for operatively connecting said pneumatic pump means and said liquid pump means to said eye-engaging infusion terminal.

5. An apparatus for substantially preventing collapse of the anterior chamber of the eye during ophthalmic surgical procedures in accordance with claim 4 wherein said cornea-engaging connection means includes external threads.

6. An apparatus for substantially preventing collapse of the anterior chamber of the eye during ophthalmic surgical procedures in accordance with claim 4 wherein said cornea-engaging connection means includes at least one annular detent.

7. An apparatus for substantially preventing collapse of the anterior chamber of the eye during ophthalmic surgical procedures in accordance with claim 4 wherein said fluid-flow connection means includes first tube means connected to said pneumatic pump means and second tube means connected to said liquid pump means, and said eye-engaging infusion terminal includes a Y-shaped terminal having a first inlet connected to said first tube means and a second inlet connected to said second tube means.

8. An apparatus for substantially preventing collapse of the anterior chamber of the eye during ophthalmic surgical procedures in accordance with claim 4 wherein said fluid-flow connection means includes first tube means connected to said pneumatic pump means, second tube means connected to said liquid pump means, third tube means connected to said eye-engaging terminal and tri-tube connection means connecting said third tube means to said first tube means and to said second tube means.

9. An apparatus for substantially preventing collapse of the anterior chamber of the eye during ophthalmic surgical procedures in accordance with claim 4 further including first valve means operatively associated with said pneumatic pump means and second valve means operatively associated with said liquid pump means.

10. An apparatus for substantially preventing collapse of the anterior chamber of the eye during ophthalmic surgical procedures in accordance with claim 4 further including foot pedal actuating means for selectively actuating said pneumatic pump means and said liquid pump means.

* * * * *

UNITED STATES PATENT OFFICE
CERTIFICATE OF CORRECTION

Patent No. 4,331,130     Dated May 25, 1982

Inventor(s) Andrew O. Lewicky

It is certified that error appears in the above-identified patent and that said Letters Patent are hereby corrected as shown below:

On the title page, the title "SECURING DEVICE TO THE CORNEA TO PREVENT ANTERIOR CHAMBER PROLAPSE" should be --DEVICE TO PREVENT ANTERIOR CHAMBER COLLAPSE--.

Signed and Sealed this

Fifth Day of October 1982

[SEAL]

Attest:

Attesting Officer

GERALD J. MOSSINGHOFF

Commissioner of Patents and Trademarks